(12) United States Patent
Tiu

(10) Patent No.: US 11,605,471 B2
(45) Date of Patent: Mar. 14, 2023

(54) SYSTEM AND METHOD FOR HEALTH CARE VIDEO CONFERENCING

(71) Applicant: Philip Tiu, Torrance, CA (US)

(72) Inventor: Philip Tiu, Torrance, CA (US)

(73) Assignee: TELEPORT INFORMATION UTILITIES, LLC, Torrance, CA (US)

(*) Notice: Subject to any disclaimer, the term of this patent is extended or adjusted under 35 U.S.C. 154(b) by 231 days.

(21) Appl. No.: 17/019,176

(22) Filed: Sep. 11, 2020

(65) Prior Publication Data

US 2022/0084690 A1    Mar. 17, 2022

(51) Int. Cl.
| | |
|---|---|
| *G16H 80/00* | (2018.01) |
| *H04L 12/18* | (2006.01) |
| *H04N 7/14* | (2006.01) |
| *H04W 4/16* | (2009.01) |
| *H04W 12/033* | (2021.01) |

(52) U.S. Cl.
CPC ......... *G16H 80/00* (2018.01); *H04L 12/1818* (2013.01); *H04L 12/1822* (2013.01); *H04N 7/147* (2013.01); *H04W 4/16* (2013.01); *H04W 12/033* (2021.01)

(58) Field of Classification Search
CPC .. H04W 12/033; H04W 4/16; H04L 12/1818; H04L 12/1822; H04N 7/147; G16H 80/00

USPC ...................................... 455/416; 348/14.02
See application file for complete search history.

(56) References Cited

U.S. PATENT DOCUMENTS

| | | | | |
|---|---|---|---|---|
| 7,835,926 | B1* | 11/2010 | Naidoo | G16Z 99/00 705/2 |
| 2008/0034085 | A1* | 2/2008 | Chawla | H04L 67/535 709/224 |
| 2016/0350721 | A1* | 12/2016 | Comerford | H04L 67/306 |
| 2019/0189292 | A1* | 6/2019 | Shaya | H04L 63/0428 |
| 2021/0399911 | A1* | 12/2021 | Jorasch | H04L 65/403 |

* cited by examiner

*Primary Examiner* — Maria El-Zoobi

(57) ABSTRACT

A method for providing video conferencing services on a mobile device is disclosed. The method may include receiving a data packet via an encrypted electronic communication channel, the data packet comprising i) authorization from a server hosting privacy health care data and ii) scheduling information for a health care provider. The method may include creating a clickable link using the data packet, the clickable link configured for initiating a video conference session from a single user action on the clickable link. The method may include, in response to the user pressing the clickable link, (i) sending a second data packet to the health care provider for initiating the video conference session, and (ii) initiating the video conference with the health care provider via a secure communication channel.

20 Claims, 19 Drawing Sheets

SYSTEM AND METHOD FOR HEALTH CARE VIDEO CONFERENCING

BACKGROUND

Field

The present disclosure relates to the field of video conference systems, and more particularly to the field of video conference systems used in a health care environment providing easy access to end users and validation of video conference sessions.

Background

Video conferencing has become popular with the migration of services online. In the health care context, providers are increasingly reliant on remote care for their patients. With the globalization of health care services, as well as novel health threats that necessitate providing care at a distance, there is long felt need for convenient video conference solutions.

Existing video conference solutions fail to adequately harmonize the technology of video conference systems with the technical computer infrastructure needed to meet the requirements of end-to-end privacy and security demanded in health care environments. Accordingly, there is a need for advanced and convenient health care video conference systems.

SUMMARY

In an aspect of the disclosure, a method implemented on a mobile video conference participant device is provided. The method may include receiving a data packet via an encrypted electronic communication channel, the data packet comprising i) authorization from a server hosting privacy health care data and ii) scheduling information for a health care provider. The method may include creating a clickable link using the data packet, the clickable link configured for initiating a video conference session from a single user action on the clickable link. The method may include: in response to the user pressing the clickable link, sending a second data packet to the health care provider for initiating the video conference session, and initiating the video conference with the health care provider via a secure communication channel. In some embodiments, once a link is established, the patient may provide consent for the system to store the linked visit data between patient and provider. This allows for future appointment requests, follow up visits, and encrypted message exchanges between patient and provider.

In another aspect of the disclosure, a method implemented on a server configured for scheduling video conference sessions is provided. The method may include receiving data associated with a patient for medical services. The method may include receiving authorization from a server hosting a database comprising privacy health care data associated with the patient in response to a query for the customer's eligibility for medical services. The method may include determining scheduling information for the patient. The method may include creating a data packet for transmission over an encrypted electronic communication channel, the data packet comprising i) the authorization from the server hosting and ii) the scheduling information. The method may include transmitting the data packet via the encrypted electronic communication channel for a remote video conference device to initiate a video conference session.

In another aspect of the disclosure, a method implemented on a mobile video conference participant device is provided. The method may include receiving data associated with a patient for medical services. The method may include receiving appointment information for the patient for medical services. The method may include receiving authorization, via an intermediate server, from an eligibility portal server hosting a database comprising privacy health care data associated with the patient in response to a query for the customer's eligibility for medical services. The method may include transmitting data to a remote mobile video conference participant device for configuration a video conference session associated with the appointment in response to receiving the authorization.

BRIEF DESCRIPTION OF THE DRAWINGS

The present disclosure is illustrated by way of example, and not by way of limitation, and may be more fully understood with reference to the following detailed description when considered in connection with the figures below.

DETAILED DESCRIPTION

Figure 1:
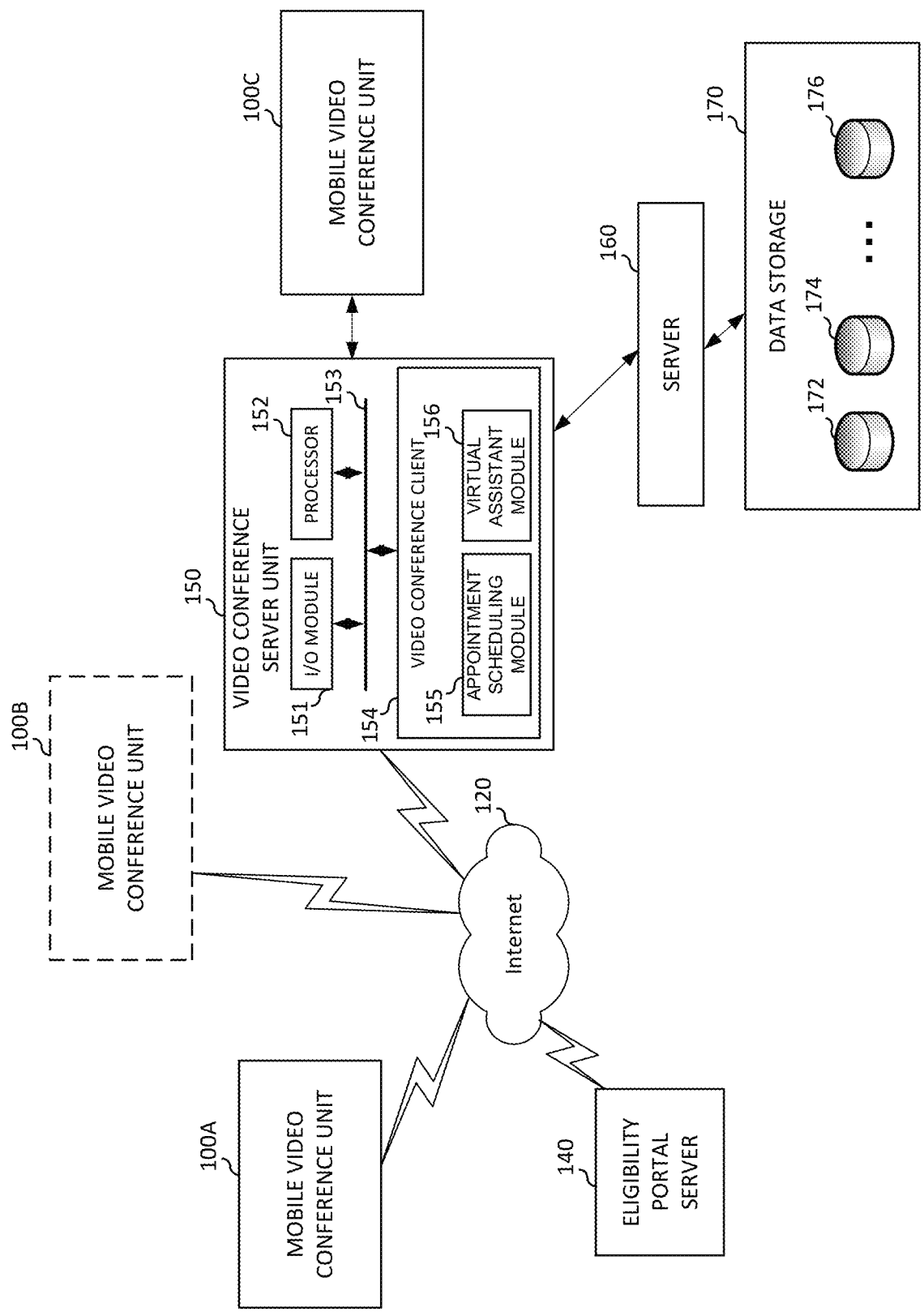
FIG. 1 is an exemplary block diagram of a system for video conferencing between video conference participant devices with the system including a video conference server unit and eligibility portal server in accordance with embodiments of the disclosure.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Methods and systems are provided for creating appointments for video conference sessions between medical providers and patients of the providers. In the disclosure, a medical provider may refer to an organization such as a hospital, medical clinic, etc. or to the individual persons such as a doctor, a nurse, or other medical provider, etc. The video conference sessions may be performed on a mobile video conference participant device. Such a mobile device may be similar to a computing device (e.g., a computer, a laptop computer, a mobile device (phone), a wearable device, or any other suitable electronic apparatus. In another example, the computing device may be a specially programmed or specially configured to be a special-purpose computing device capable of performing the methods disclosed herein. Advantages disclosed herein include enabling simple and reliable communication between patients and their medical providers. The methods enable collection of patient data (e.g., data entry from either the patient or the medical provider) and interfacing to an eligibility portal (e.g., via secure communications with a server including eligibility information) to set up one-click video conferencing for patients. For example, the medical provider may provide all patient information and appointment scheduling information into a video conference participant device or a video conference participant server with the device or server communicating with the eligibility portal to determine entitlement to the services. Once the entitlement is determined, but device or server may send information (e.g., a data packet including all necessary information) to the patient's video conference participant device to set up a one-click link for the patient. In this manner, a video conference session for a medical video conference appointment is created without manual input of data into a device of the client prior to joining the video conference session.

In some embodiments, the systems and methods may provide for mobile clinical staff (MCS) scheduler integration. For example, certain specialties may need to incorporate the services of MCS to facilitate an upcoming video conference visit. MCS may be a separate on-site service system, either freelance-based or employer-managed company that may complement these video conference visits by sending one or more MCS to patient's home prior to or during a video conference session. MCS can be one or combination of medical assistant, emergency medical technician (EMT), patient care tech, medical technician, lab tech or IT tech, depending on practice needs. They may bring portable video conference kits which may include: laptop with Wi-Fi hotspot or satellite internet, point-of-care equipment for vitals, glucometers, venipuncture kits, blood pressure cuffs, otoscopes and other designed scopes for heart and lung sounds or even skin irregularities. Each practice may assess their own triage protocols to identity and customize their MCS needs. Practices, health plans or managed care groups may need to contract with an MCS deployment company or engage in a pay-as-you-go option.

Reference is now made to FIG. 1, which illustrates a system enabling features associated with enabling video conference sessions between medical providers and patients using the video conference participant devices 100A-C. For example, the features may configure the system for scheduling patient appointments with medical providers, which may include patient interactions such as receiving biographical and entitlement information, receiving appointment scheduling information, or reading biometric signals of the patient. The features may include interfacing with an eligibility portal server (e.g., a universal eligibility portal (ELI)) to determine the (e.g., types and scope of) medical services available to the patients.

In some embodiments, the video conference participant devices may be facilitated by a video conference server unit 150, with at least one video conference unit 100C linked to the video conference server unit 150 within a local area network such as a medical clinic or hospital; the video conference server unit 150 may facilitate video conference sessions between, e.g., video conference participant devices 100A, 100C.

In other optional embodiments, the video conference unit 100B may be in communication with the video conference server unit 150 via the internet, with the video conference server unit 150 facilitating the video conference sessions. In yet other embodiments, the video conference units (e.g., 100A, 100B) may include functionality to facilitate the video conference sessions between themselves without needing a video conference server unit 150. In such embodiments, one of the video conference units (e.g., 100B) may include server capabilities such as communication with the eligibility portal server 140.

The system may include a data store 170 (e.g., databases 172, 174, . . . , 176) for storing video conference session data and metadata. The video conference server unit 150 (or one of the mobile video conference units 100B, C, may be in communication with the server 160 to store data associated with the video conference sessions. For example, the video and audio itself may be stored. In another example, metadata such as the appointment dates, times, participants, etc. may be recorded to provide a log of the sessions. In some embodiments, the logs and records may be saved and configured based on medical rules such as the Health Insurance Portability and Accountability Act (HIPPA).

In some embodiments, the system may provide end-to-end encryption for private and secure communications. Any suitable encryption schemes such as RSA private key, public key, pre-shared keys, etc. may be used to provide the end-to-end encryption. In some embodiments, a server or module within of the processing units such as video conference service unit 150 may provide features to enable encryption of the communication. For example, server 160 (or a module) may be an encryption or authentication server. The encryption or authentication server may authenticate user passwords and/or grant access to network resources (e.g., other servers) and/or network services, and provide for encryption of end-to-end messages. An authentication server may also provide an access ticket (e.g., a Kerberos Ticket Granting Ticket (TGT)) to a client (e.g., a computing system 101) after authentication of the user password. The access ticket (e.g., a TGT) may be used to access network locations, network resources, and/or network services. In another embodiment, the authentication server may be part of a Single Sign-On (SSO) system. In an SSO system, a user is generally authenticated by the authentication server and the authentication server grants access (e.g., via a TGT) to multiple devices, network resources, network locations, and/or network services, which use the SSO system for authentication. In will be readily apparent to one skilled in the art that other encryption and authentication methods may be used with the embodiments of the disclosure. For example, the disclosure is not limited to the Kerberos or SSO methods and systems. Other examples may include multi-factor encryption and authentication, public key or private key encryption, etc. Authorization, Authentication, and Access (AAA) servers may be used in various embodiments of the disclosure. One skilled in the art will recognize that any of these servers may be placed at various logical or physical locations; for example, the encryption and/or authentication server may be located between the user mobile devices (e.g., 100A-C) and video conference server unit 150.

The mobile video conference units 100A, B may include a module for providing the end-to-end encryption. For example, a module within the mobile video conference units 100A, B may include software and/or hardware for communication using encrypted messaging with other mobile video conference units 100A, B or video conference server unit 150.

In accordance with an exemplary embodiment, the user of video conference participant device 100A may share his video, audio, biometric information with the other participants. Audio/video from video conference participant device 100 may be forwarded to video conference server 200 via the Internet 120 and/or any other suitable communication network such as, for example but not limited to, a wide area network (WAN), a local area network (LAN), a mobile communication network, a satellite communication link, a landline telephone service, etc.

Video conference server 150 may include processor 152, I/O module 151, data bus 153, and video conference application 154. It will be appreciated that video conference server 150 may include hardware and software components, such as are well-known in the art. It will similarly be appreciated video conference server 150 may include other components are not depicted in FIG. 1. Video conference server 150 may include more than one process 152. For example, one such process 152 may be a special purpose processor operative to execute video conference client 154. Video conference client 154 may be an application that is implemented in software and/or hardware on video conference serve 150. Video conference client 154 may be any suitable server-side application for video conferencing including commercial off-the-shelf software from a software vendor or may be purpose-built software. In accordance with embodiments described herein, video conference application 154 may include an appointment schedule module 155 configured for determining appointment dates and sessions between patients and the medical providers. Video conference client 154 may include a virtual assistant module 156 configured for provide virtual assistant to the users such as the patients or medical provider staff. In some embodiments, the virtual assistant may be based on an artificial intelligence (AI) model. The AI model may be configured based on any one of the suitable AI techniques including neural networks, deep learning modeling, natural language processing, etc. In some embodiments, the AI model may be configured by another processing unit (e.g., a dedicated or distributed processing server) with the tailored AI model copied to the video conference server unit.

I/O module 151 may be a hardware and/or software component that may be configured to transmit and receive data to and from devices in communication with video conference unit 150. In some embodiments, I/O module 151 may include encryption algorithms to provide secure end-to-end communications with mobile devices such as 100A-C. In other embodiments, a separate module (not shown) coupled to the processor may be configuration to provide the encryption algorithms to provide secure end-to-end communications.

For example, I/O module 151 may be implemented as a transceiver. Video conference server 150 may be configured to use I/O module 151 to facilitate a video conference session between users of video conference participant devices 100 as per instructions received from video conference client 154.

It will be appreciated that each of video conference devices 100A-C may be configured and implemented in accordance with any of the configurations described herein with relation to video conference participant device 100.

Figure 2:
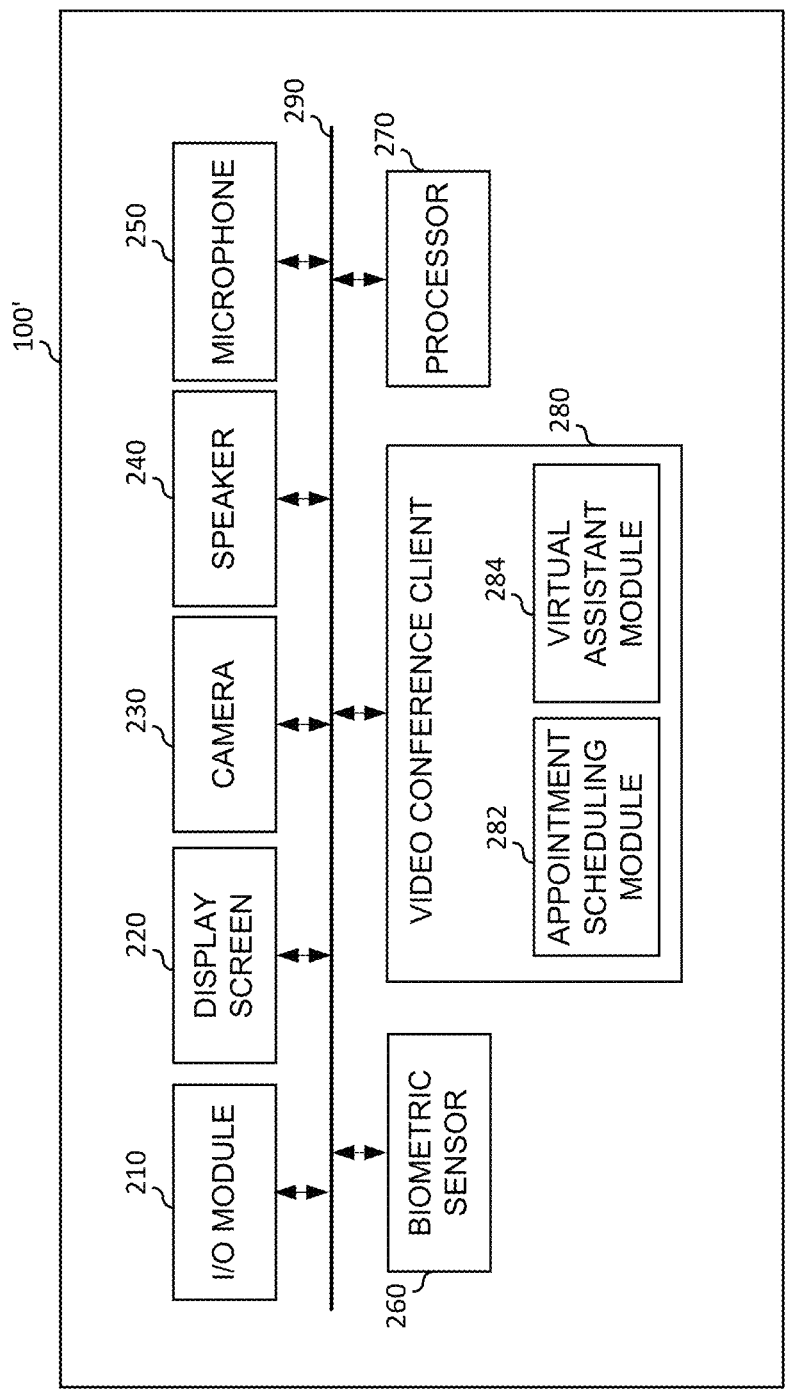
FIG. 2 is an exemplary block diagram of the video conference participant device of FIG. 1.

FIG. 2 is an exemplary block diagram of the video conference participant device of FIG. 1. Video conference participant device 100' may include processor 270, I/O module 210, display screen 220, camera 230, one or more speakers 240, microphone 250, biometric device 260, data bus 290 used for communication between the components, and video conference client 280, which may be implemented as either a software application and/or hardware component and may be executable by processor 270 to facilitate participation by video conference participant device 100' in a video conference meeting such as depicted in FIG. 1. Processor 270 may also operate I/O module 210, display screen 220, camera 230, speaker 240, microphone 250, and biometric sensor 260 in support of video conference meetings as per instructions provided by video conference client 280. For example, I/O module 210 may send and receive audio/video data between the participants of the video conference meeting; received video data may be displayed on display screen 220; camera 230 may provide video data to be sent to other video conference participant devices 100'; speaker(s) 240 may play the received audio data; microphone 250 may provide audio input to be sent to other video conference participant devices 100'; and biometric sensor(s) 260 may read biometric data from a user (e.g., a patient) of the device 100' to send to another participant device 100' (e.g., a medical provider viewing and interpreting the biometric data). In some embodiments, I/O module 210 may include encryption algorithms to provide secure end-to-end communications with other mobile devices or servers units such as video conference server unit 150. In other embodiments, a separate module (not shown) coupled to the processor 270 may be configuration to provide the encryption algorithms to provide secure end-to-end communications.

In some embodiments, the video conference sessions may be between two video conference participant devices such as between a doctor and a patient; in other embodiments video conference sessions may be created among a group of more than two participants. For example, a video conference session may include more than one medical provider (e.g., one doctor plus one nurse, two doctors, etc.) or may include more than one patient.

In accordance with embodiments described herein, video conference client 280 may include an appointment scheduling module 282. Appointment scheduling module 282 may be implementable either as a software application and/or hardware component that may be implemented as either an integrated component of video conference client 280 or as an independent module in communication with video conference client 280. As will be described below, appointment scheduling module 282 may be configured to perform scheduling routines on video conference participation device 100'. When the video conference participant device is used by a user (e.g., a patient), the appointment scheduling routines may be configured, for example, for gathering information from the user, and for alerting the user that an appointment has been scheduled. When the video conference participant device 100' is used by a medical provider, the appointment scheduling routines may gather appointment scheduling information and patient information to determine an appropriate appointment date and time for the video conference session. In other embodiments, the appointment scheduling module 282 may be included in the video conference server unit as illustrated in FIG. 1.

Video conference client 280 may include a virtual assistant module 284. Virtual assistant module 284 may be implementable either as a software application and/or hardware component that may be implemented as either an integrated component of video conference client 280 or as an independent module in communication with video conference client 280. As will be described below, virtual assistant module 284 may be configured to perform virtual assistant functions such as interacting with a user (e.g., a patient or a medical provider) on the video conference participation device 100'. Such interactions, for example, may include answering user queries or questions, and the interactions may include gather information from the user to send to the appointment scheduling module 282. When the video conference participant device 100' is used by a medical provider, the virtual assistant module 284 may provide answers regarding patient information or other general provider-side information. Virtual assistant module 284 may work in conjunction with the appointment scheduling module 282 to determine appropriate appointment dates and times for video conference sessions.

Virtual assistant module 284 may include software and/or hardware for creating the AI model used to interact with the user. In other embodiments, the AI model may be previously created (e.g., at a dedicated or distributed processing node(s)) with the resulting model copied to the module 284.

Figure 3A:
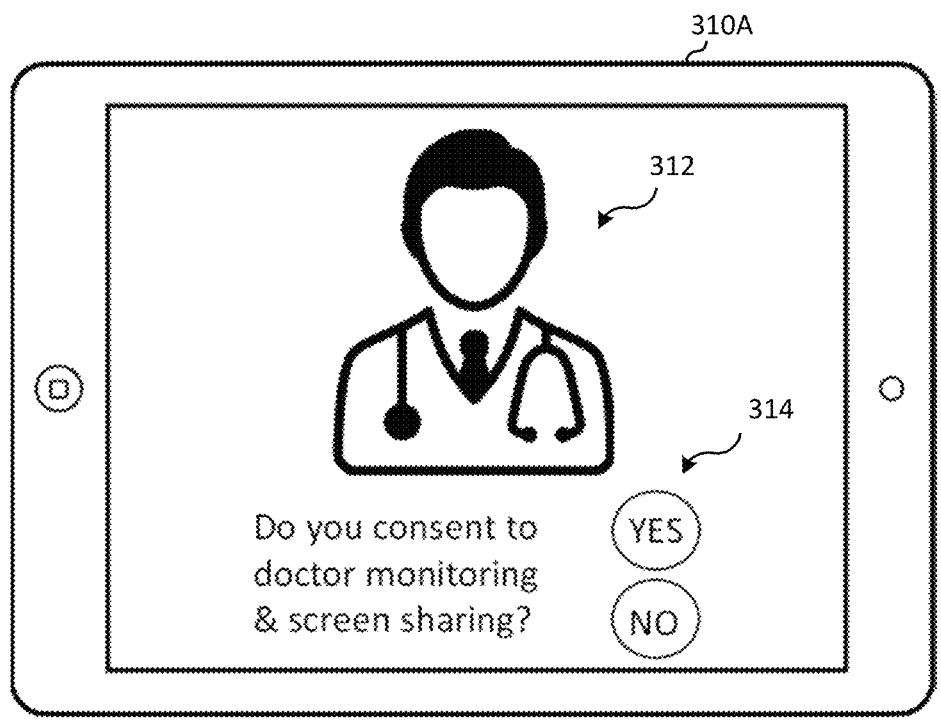
FIGS. 3A-B are further exemplary diagrams illustrating display screens of the video conference participant device as viewed from a patient user of the system.
Figure 3B:
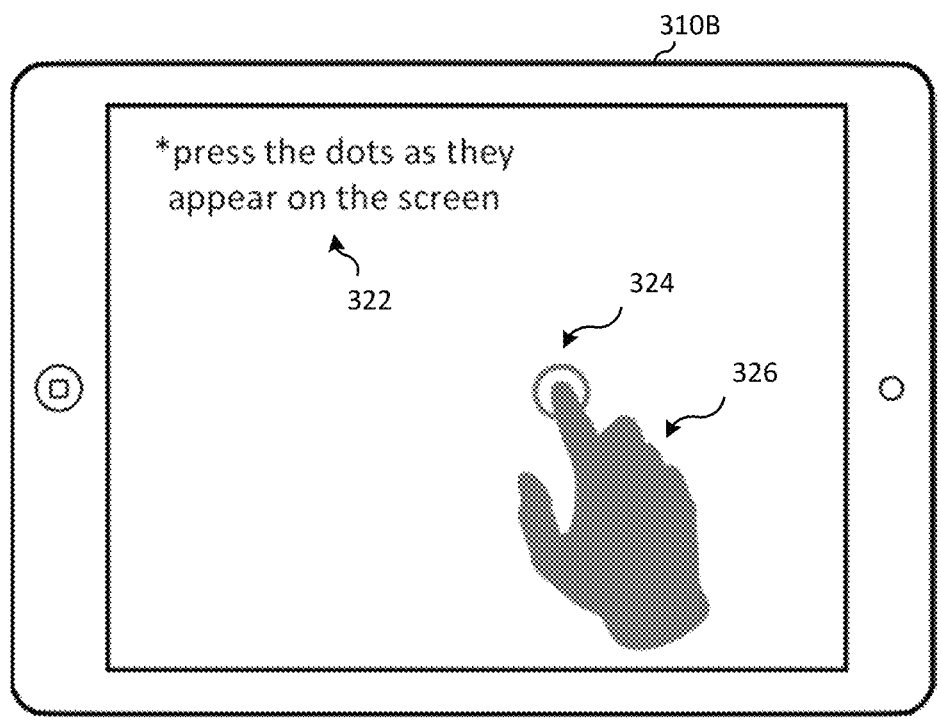

FIGS. 3A-B are further exemplary diagrams illustrating display screens of the video conference participant device of FIG. 2 as viewed from a patient user of the system. For example, the video conference participant device 310A may be a mobile table device, smart phone, wearable device, etc. The screen of the device 310A shows an example video conference session with the other participant being a doctor 312. The user may be provided with various prompts 314 such as whether to consent to sharing the screen.

In some embodiments as shown in FIG. 3B, the device 310B may include game-like interfaces for maintaining the attention of the user. These interfaces may be suitable for younger patients who may lose focus during a video conference session. Such interfaces may also provide feedback regarding the user's mental states (e.g., their mental or physical reflexes). In the example of FIG. 3B, the doctor may have switched the user's display to a game-like interface for keeping the attention of the user 326. An example game-like interface may include a caption 322 requesting the user 326 to tap the screen as objects or dots 324 appear on the device 310B. FIG. 3B shows the user 326 engaged and taping on the flashing dot 324.

It will be appreciated to one skilled in the art that any of various games or applications may be suitable for maintaining (or in some cases distracting) the user's focus on the current session.

Figure 4:
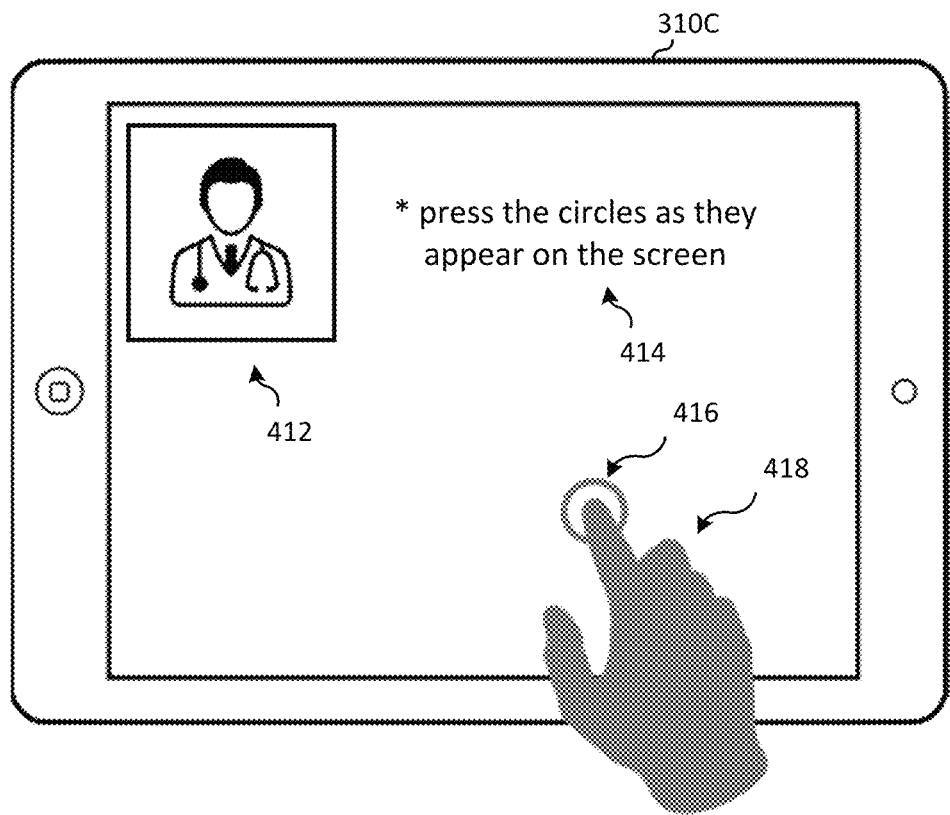
FIG. 4 is another exemplary diagram illustrating a display screen of the video conference participant device as viewed from a patient user of the system.

FIG. 4 is another exemplary diagram illustrating a display screen of the video conference participant device 310C as viewed from a patient user of the system. In the example screen, the doctor 412 is shown in a split-screen format with the game-like interface occupying the remainder of the screen. The game-like interface may include a caption 414 requesting the user 418 to tap the screen as objects or dots 416 appear on the device 310C. FIG. 4 shows the user 418 engaged and taping on the flashing dot 416.

Figure 5:
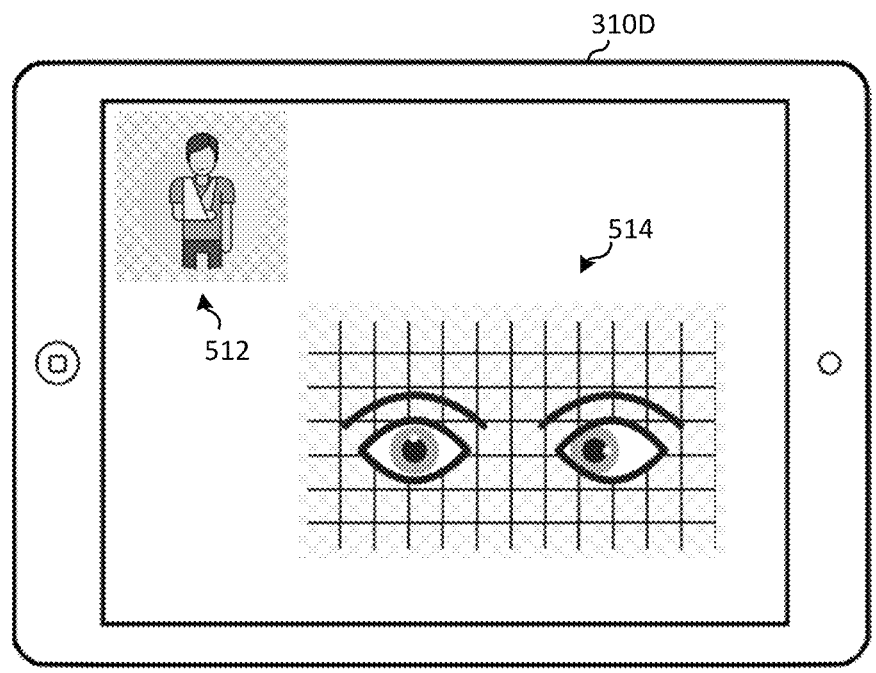
FIG. 5 is another exemplary diagram illustrating a display screen of the video conference participant device as viewed from a medical provider user of the system.

FIG. 5 is another exemplary diagram illustrating a display screen of the video conference participant device 310D as viewed from a medical provider user of the system. During a video conference session, the medical provider user may have access to various display options. Some of the display options may include data views (e.g., patient information, biometric information, etc.), live (real-time) views of the patient, etc. Any number of these displays or views may be shown at a time on the medical provider device 310D. In the example of FIG. 5, the device 310D shows two views on the device 310D including a view of the patient 512 and a view of biometric information 514, which is eye biometrics in this example.

Figure 6A:
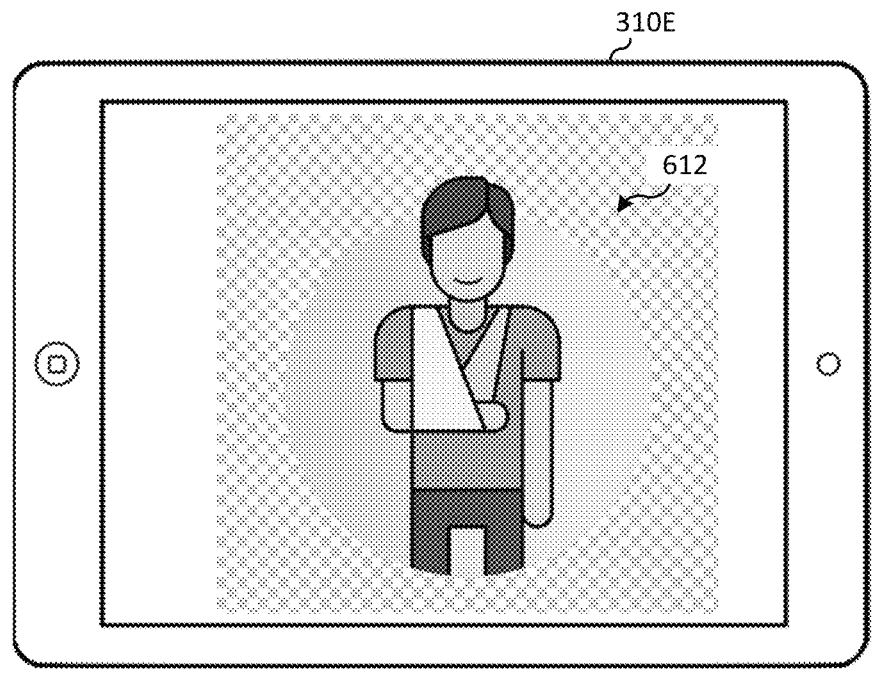
FIGS. 6A-B are further exemplary diagrams illustrating display screens of the video conference participant device as viewed from a medical provider user of the system.
Figure 6B:
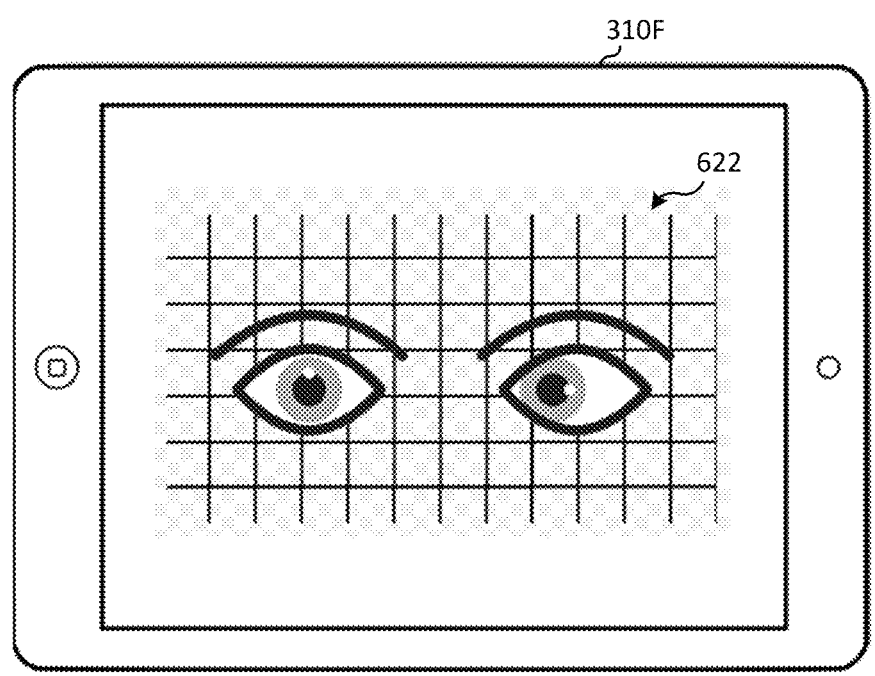

FIGS. 6A-B are further exemplary diagrams illustrating display screens of the video conference participant device 310E as viewed from a medical provider user of the system. In the example of FIG. 6A, the device 310E shows a single view with a live video 612 of the patient. The live video 612 may provide a similar experience to an in-person doctor's visit. The video conference device 310E may use biometric sensors such as heart rate monitors, fingerprint readers, oximeters, etc. to provide readings and data. In the example of FIG. 6B, the device 310F screen shows eye biometrics 622 for the medical provider to make an assessment of the patient. It will be appreciated by those skilled in art that any number and type of visual screens may be available to and chosen by the medical provider as suitable.

Figure 7:
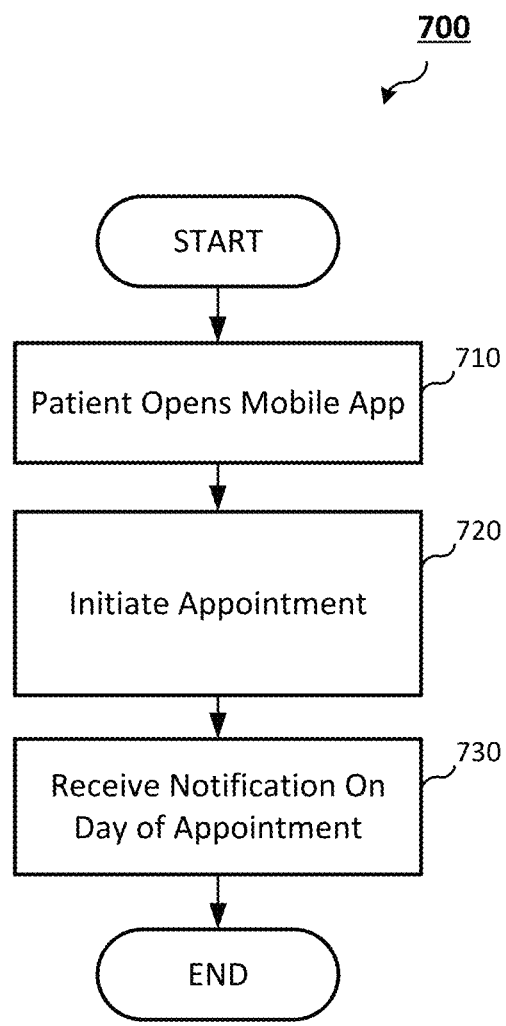
FIG. 7 is an exemplary flow diagram illustrating methods for initiating an appointment for a video conference session from the perspective of a patient user of the system.

FIG. 7 is an exemplary flow diagram illustrating methods for initiating an appointment for a video conference session from the perspective of a patient user of the system. The method may be performed by a mobile device, such as video conference participant devices 100A-C of FIG. 1 or 100' of FIG. 2. The method may be methods of the video conference client 100' and/or the appointment scheduling module 282. Starting at 710, the method may include a user (e.g., patient) opening the video conference client mobile application. For example, the user may launch the software application on the mobile device; in other embodiments, the mobile device may be a dedicated platform and opening the software application may be automatic once the mobile device is in an "on" state. The step 720, the method may include initiating an appointment. Initiating an appointment may include scheduling a time and date for a medical visit via video conference. At step 730, the method may include receiving notification on the day of the appointment. In some embodiments, the user performing only a single step of clicking on a link that starts a video conference session with a medical provider, with the link crafted by the video conference client based on data received from a remote server or a remote video conference client. For example, the video conference server unit 150 of FIG. 1 or the mobile video conference unit 100B may be determined services entitlement along with appointment scheduling information to transmitted a set of data to the mobile device; based on the transmitted set of data, the mobile device crafts a link for the user.

Figure 8:
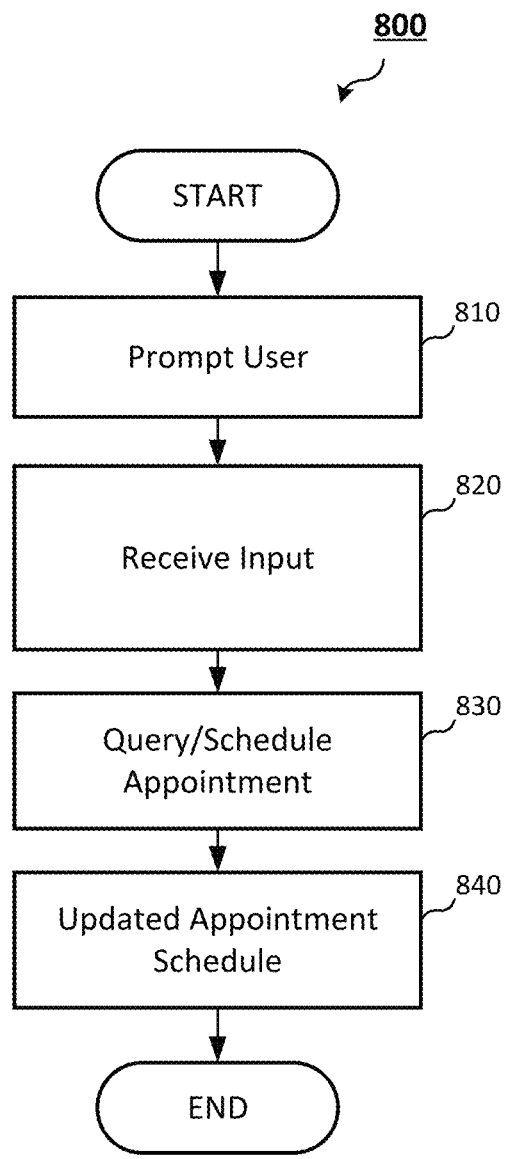
FIG. 8 is another exemplary flow diagram illustrating methods for updating an appointment for a video conference session from the perspective of a patient user of the system.

FIG. 8 is another exemplary flow diagram illustrating methods for updating an appointment for a video conference session from the perspective of a patient user of the system. The method may be performed by a mobile device, such as video conference participant devices 100A-C of FIG. 1 or 100' of FIG. 2. The method may be methods of the video conference client 280 and/or the appointment scheduling module 282. Starting at 810, the method may include prompting a user for information. For example, the device may prompt for biographical information, medical history, insurance plan information, user preferences for medical providers, etc. At step 820 the method may include receiving the input. At step 830 at the method may include querying or scheduling an appointment. Querying for or scheduling an appointment may include the device communicating with a remote server such as server 150 of FIG. 1 or a remote mobile device conference unit such as 100B of FIG. 1. At step 840, the method may include updating the appointment schedule. For example, may be a response from the remote device based on the query, the method may include the user's mobile device updating a local calendar with the appointment information.

Figure 9:
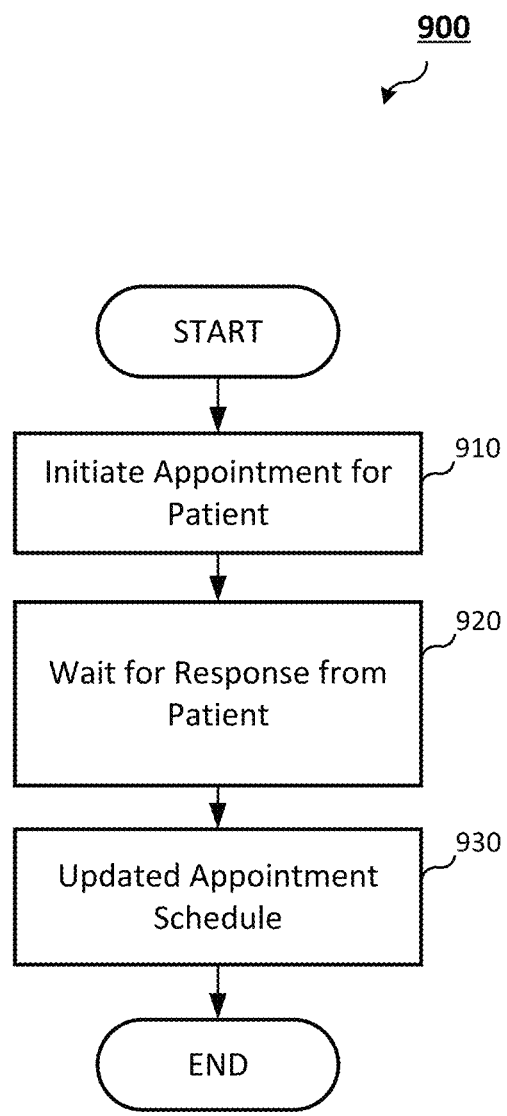
FIG. 9 is another exemplary flow diagram illustrating methods for updating an appointment for a video conference session from the perspective of a patient user of the system.

FIG. 9 is another exemplary flow diagram illustrating methods for updating an appointment for a video conference session from the perspective of a patient user of the system. The method may be performed by a mobile device, such as video conference participant devices 100A-C of FIG. 1 or 100' of FIG. 2. The method may be methods of the video conference client 280 and/or the appointment scheduling module 282. Starting at step 910, the method may include initiating an appointment for the user (e.g., patient). At step 920, the method may include waiting for a response from the user (e.g., patient). At step 930, the method may include updating the appointment schedule.

Figure 10:
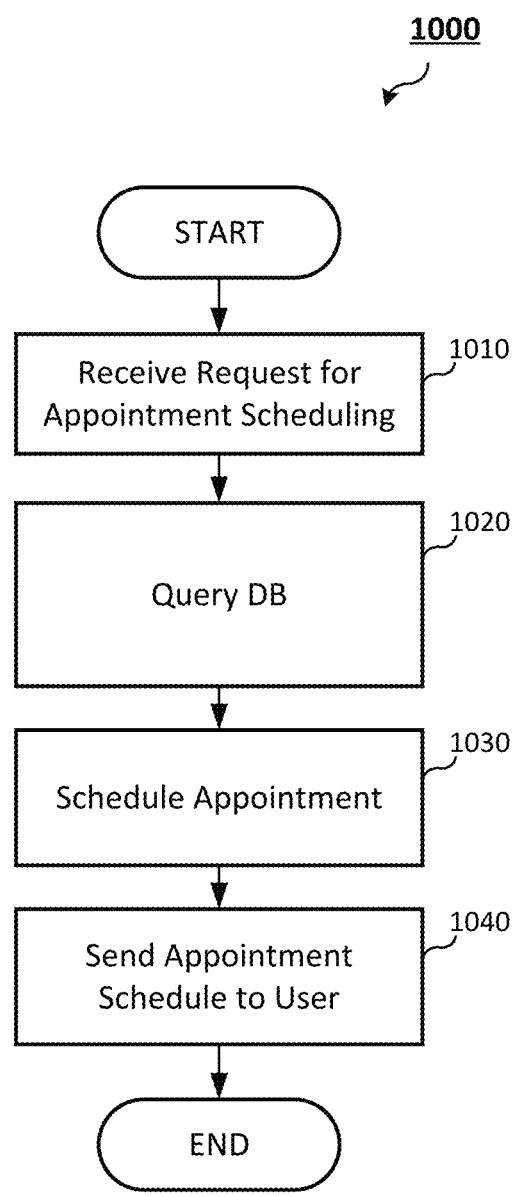
FIG. 10 is another exemplary flow diagram illustrating methods for scheduling and sending an appointment for a video conference session from the perspective of a medical provider user of the system.

FIG. 10 is another exemplary flow diagram illustrating methods for creating a single step one-click link to initiate a video conference session from the perspective of a medical provider user of the system. The method may be performed by a mobile device, such as video conference participant devices 100A-C of FIG. 1 or 100' of FIG. 2. The method may be methods of the video conference client 280 and/or the appointment scheduling module 282. Starting at 1010, the method may include receiving a request for appointment scheduling. For example, after a user of a remote mobile device requests an appointment, the medical provider user may receive the indication for an appointment. At step 1020, the method may include querying a database. For example, the method may include querying a remote server hosting eligibility information for the patient. At step 1030, the method may include determining the date and time to schedule the appointment. The scheduling may be based on one of several factors including the patient availability, medical provider availability, etc. At step 1040, the method may include sending the appointment schedule to the user (e.g., patient) at a remote device. For example, the method may transmit a set of data including the scheduling appointment and any other information necessary for the remote device to join the video conference session on the date of the appointment.

Figure 11:
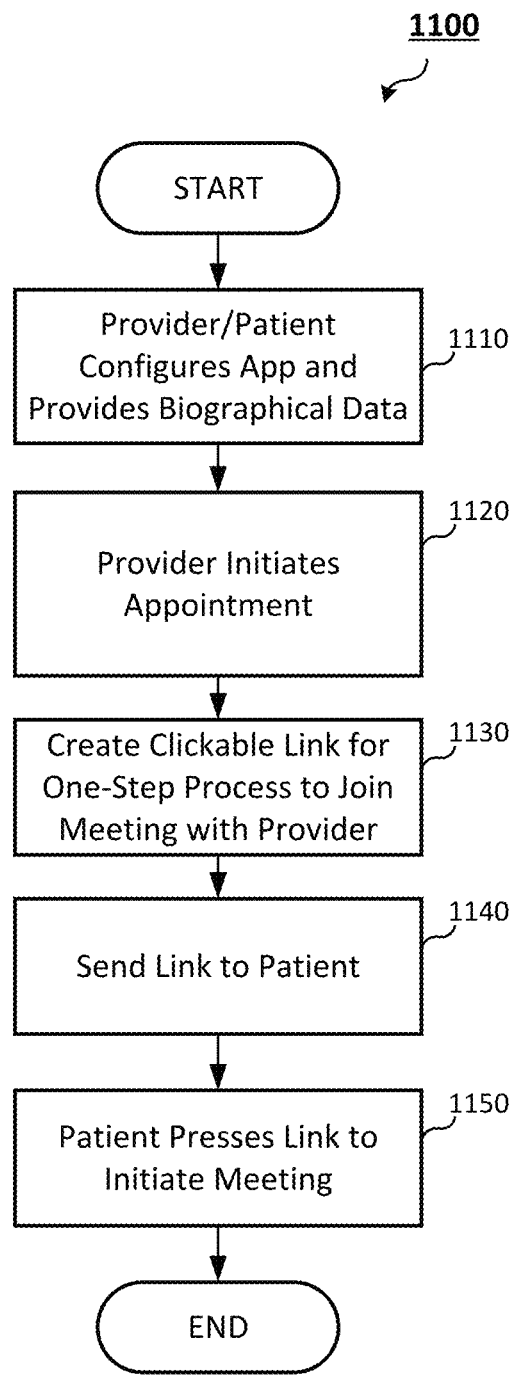
FIG. 11 is another exemplary flow diagram illustrating methods for creating a single step one-click link to initiate a video conference session from the perspective of a medical provider user of the system.

FIG. 11 is another exemplary flow diagram illustrating methods for scheduling and sending an appointment for a video conference session from the perspective of a medical provider user of the system. The method may be performed by a mobile device, such as video conference participant devices 100A-C of FIG. 1 or 100' of FIG. 2. The method may be methods of the video conference client 280 and/or the appointment scheduling module 282. Starting at 1110, the method may include the provider or patient configuration the mobile application and providing the patient's information, such as biographical data. At step 1120, the method may include the provider initiating an appointment. At step 1130, the method may include creating a clickable link for a one-step process to join a video conference session (i.e., an online meeting) with the medical provider. At step 1140, the method may include sending the link to the patient. At step 1150, the method may include the patient pressing the link to initiating the meeting.

Figure 12:
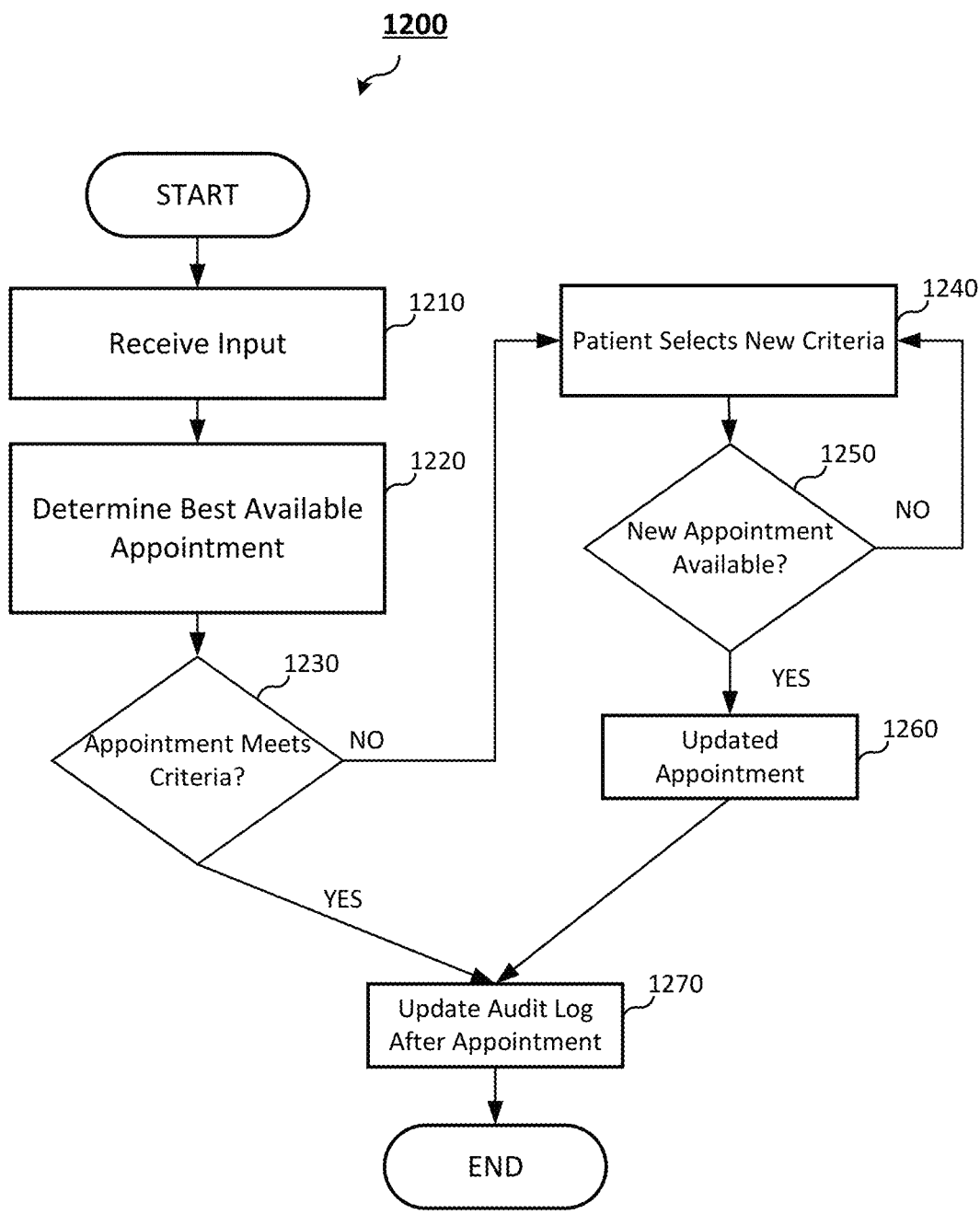
FIG. 12 is another exemplary flow diagram illustrating methods for creating an appointment for a video conference session.

FIG. 12 is another exemplary flow diagram illustrating methods for scheduling and sending an appointment for a video conference session from the perspective of a medical provider user of the system. The method may be performed by a mobile device, such as video conference participant devices 100A-C of FIG. 1 or 100' of FIG. 2. Starting at 1210, the method may include receiving input from a patient and/or a medical provider relating to a medical visit. The information from the patient and/or medical provider may include preferences for the scheduling such as time slots, preferred doctors or other medical professionals, etc. At step 1220, the method may include determining a best available appointment schedule. For example, based on the input received from the patient, the method selects a best available appointment. At step 1230, the method may determine whether the appointment meets a set of criteria. For example, the patient may have specified preferred time and date slots for the appointment, but the medical provider has limited available such that the scheduled appointment date and time does not meet at least of the patient or medical provider's criterion. If the scheduled appointment meets the criteria then the method may proceed to step 1270. If the scheduled appointment does not meet at least one criterion then the method may proceed to step 1240. At step 1240 the patient may select new criteria for the appointment. At step 1250 the method may determine whether a new appointment is available. For example, the method may determine whether a new appointment is available that meets the criteria. For example, the patient may have specified new time slots for appointment availability. The method may determine whether an appointment is available that meets the patient's availability. If a new appointment is available, then the method may proceed to step 1260. If a new appointment is not available, then the method may proceed back to step 1240. In some embodiments, the method may continuously loop back to prompt the patient for new criteria. At step 1260, the method may include updating the appointment information based on the new available appointment. At step 1270, the method may update an audit log after the appointment.

Figure 13:
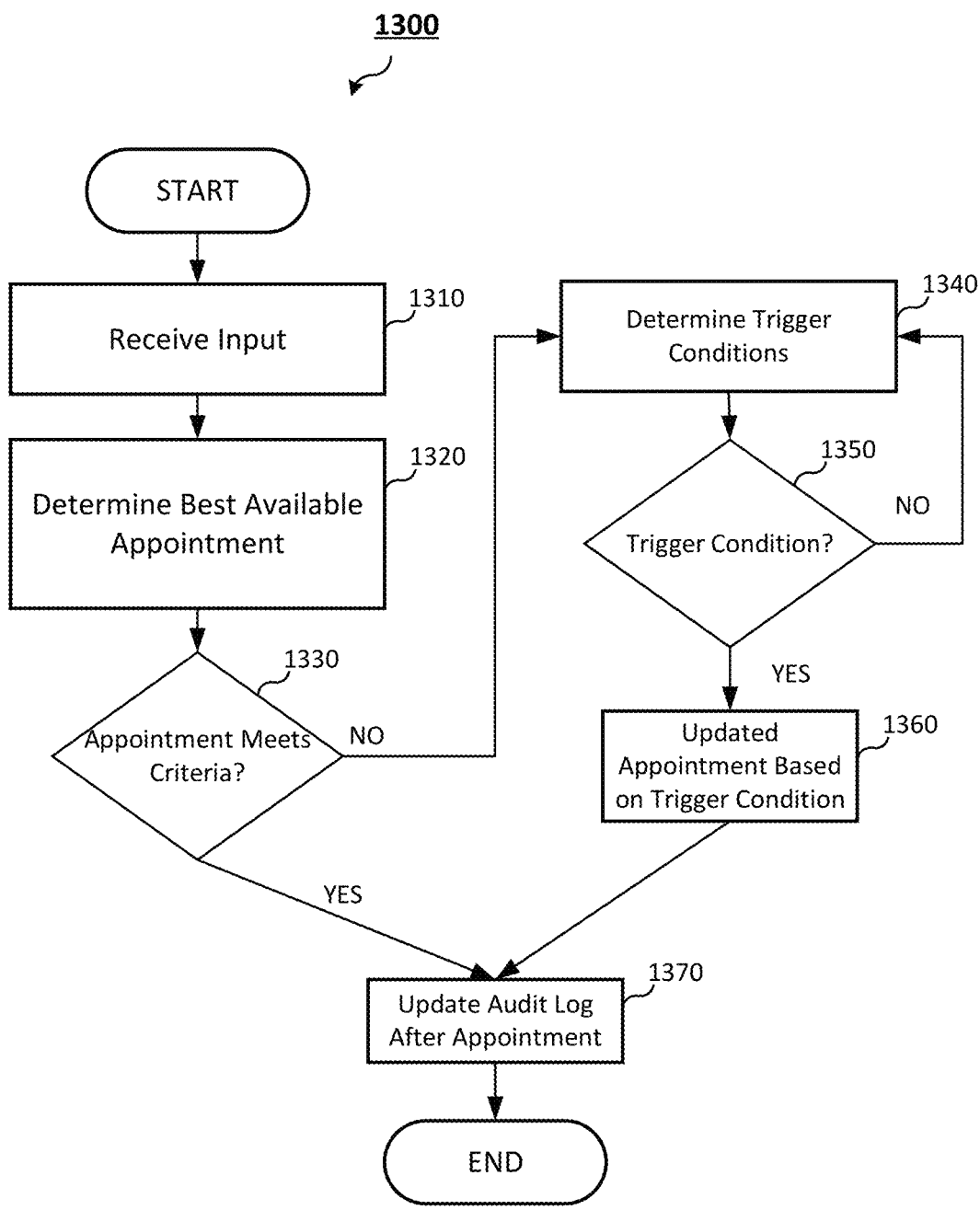
FIG. 13 is another exemplary flow diagram illustrating methods for creating an appointment for a video conference session.

FIG. 13 is another exemplary flow diagram illustrating methods for creating an appointment for a video conference session. The method may be performed by a mobile device, such as video conference participant devices 100A-C of FIG. 1 or 100' of FIG. 2. Starting at 1310, the method may include receiving input from a patient and/or a medical provider relating to a medical visit. The information from the patient and/or medical provider may include preferences for the scheduling such as time slots, preferred doctors or other medical professionals, etc. At step 1320, the method may include determining a best available appointment schedule. For example, based on the input received from the patient, the method selects a best available appointment. At step 1330, the method may determine whether the appointment meets a set of criteria. For example, the patient may have specified preferred time and date slots for the appointment, but the medical provider has limited available such that the scheduled appointment date and time does not meet at least of the patient or medical provider's criterion. If the scheduled appointment meets the criteria then the method may proceed to step 1370. If the scheduled appointment does not meet at least one criterion then the method may proceed to step 1340. At step 1340 the method may determine at least one trigger condition for scheduling or rescheduling the appointment. For example, trigger conditions may include time-based triggers, new slot times becoming available from the medical provider, new services eligibility for the patient, etc. At step 1350, the method may determine whether at least one trigger condition has been set. For example, a trigger condition may be an elapsed time. If the elapsed time is met, the method may determine a new best available appointment. In another example, a trigger condition may be availability of a medical provider. If the medical provider has new availability, the method may determine a new best available appointment. If the at least one trigger condition is not set, then the method may proceed back to step 1340. In some embodiments, the method may loop until the at least one trigger condition is set, and then proceed to step 1360. If at least one trigger condition is set, then the method may proceed to step 1360. At step 1360, the method may include updating the appointment based on the at least one trigger condition. At step 1370, the method may update an audit log after the appointment.

Figure 14A:
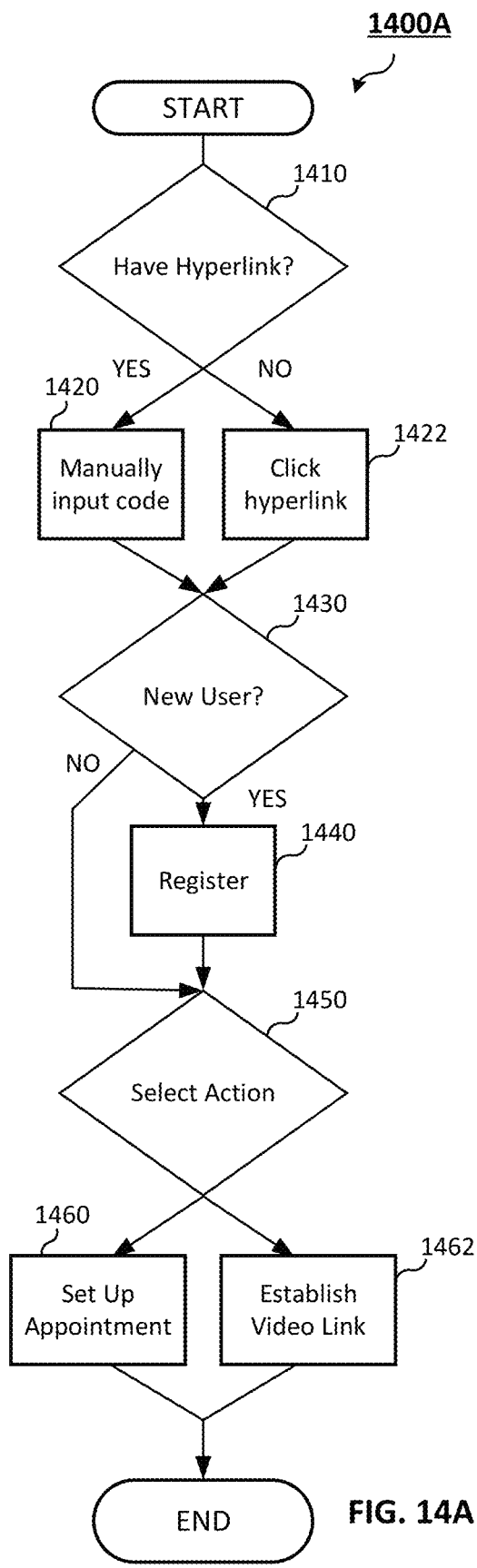
FIGS. 14A-B are further exemplary flow diagrams illustrating methods for establishing and initiating an appointment for a video conference session.
Figure 14B:
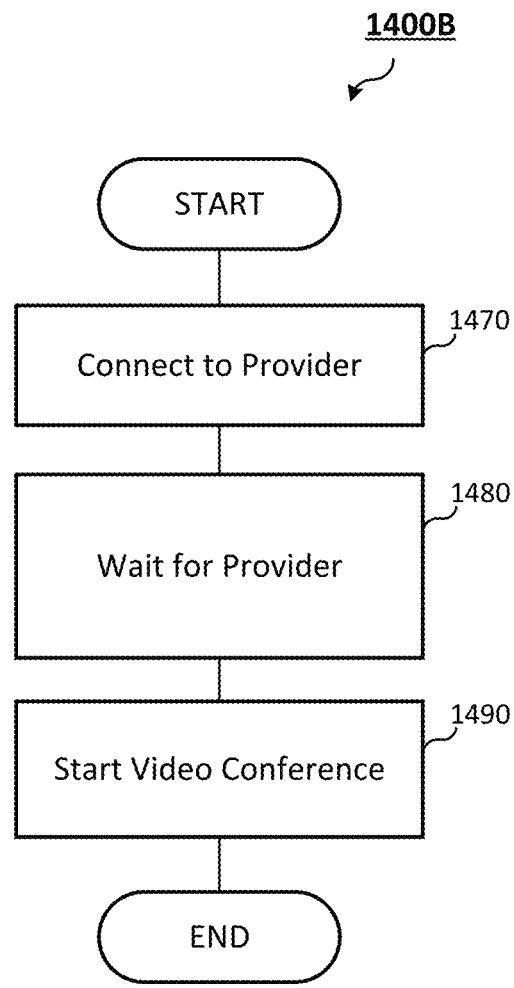

FIGS. 14A-B are further exemplary flow diagrams illustrating methods for establishing and initiating an appointment for a video conference session. The method may be performed by a mobile device, such as video conference participant devices 100A-C of FIG. 1 or 100' of FIG. 2. Beginning at step 1410, the method may include determining whether the user has a hyperlink for a video conference meeting. For example, the user's own device may have crafted a hyperlink for the video conference session, or the user's device may have received a hyperlink from the remote server or a remote device to join the video conference session. The hyperlink may reflect previous queries to an eligibility server to determining entitled for medical services for the user. The hyperlink may represent a single-step process; in some embodiments, this single-step process may have been created without the user without having entered the various medical and/or biographical information. In other embodiments, the user may have entered basic information prior to any needing for medical attention; in such instances, the single-step process may represent a simplified process without the user need to take any actions between providing the basic information and receiving the hyperlink for the video conference session. For example, either the user or the medical providers may have determined a need for a medical visit via teleconference. The medical providers may have completed data entry of their devices, with a server or the medical provider's devices sending a hyperlink to the user for the video conference session. One skilled in the art will appreciate that alternatives to a hyperlink may be suitable based on design choices. If the user does not have a hyperlink then the method may proceed to step 1420. If the user has a hyperlink then the method may proceed to step 1422.

At step 1420, the user may manually enter a code for a video conference session. For example, the user may have received a code via email, text message, or the like for the video conferences session. The user may enter the code to initiate the video conference session.

At step 1422, the user clicks on the hyperlink. In other embodiments the action may be based on clicking on some graphical user interface component such as a button where the devices may be in secure communication over a proprietary protocol.

At step 1430, the method may determine whether the user is new to the platform and application. If the user is new, the method may proceed to step 1440. If the user has previously used the application or has previously registered with the application, then the method may proceed to step 1450. At step 1440, the user may register with the application. For example, the user may provide biographical data to the application. The user may also provide preferences for scheduling appointments such as preferred date and time slots, preferred medical providers, location preferences, etc.

At step 1450, the user may select an available action from the application. The available actions may include those related to setting up or establishing a video link. The available actions may include entering information for the user. At step 1460, the method may include setting up an appointment. For example, the user may request an appointment and provide information for setting up the appointment. At step 1462, the method may include establishing a video link.

In another process 1400B, the method may start at 1470 to connect to a provider (e.g., a medical provider). The method may include, at step 1480, waiting for the provider. At method may include, at step 1490, starting a video conference session.

Figure 15:
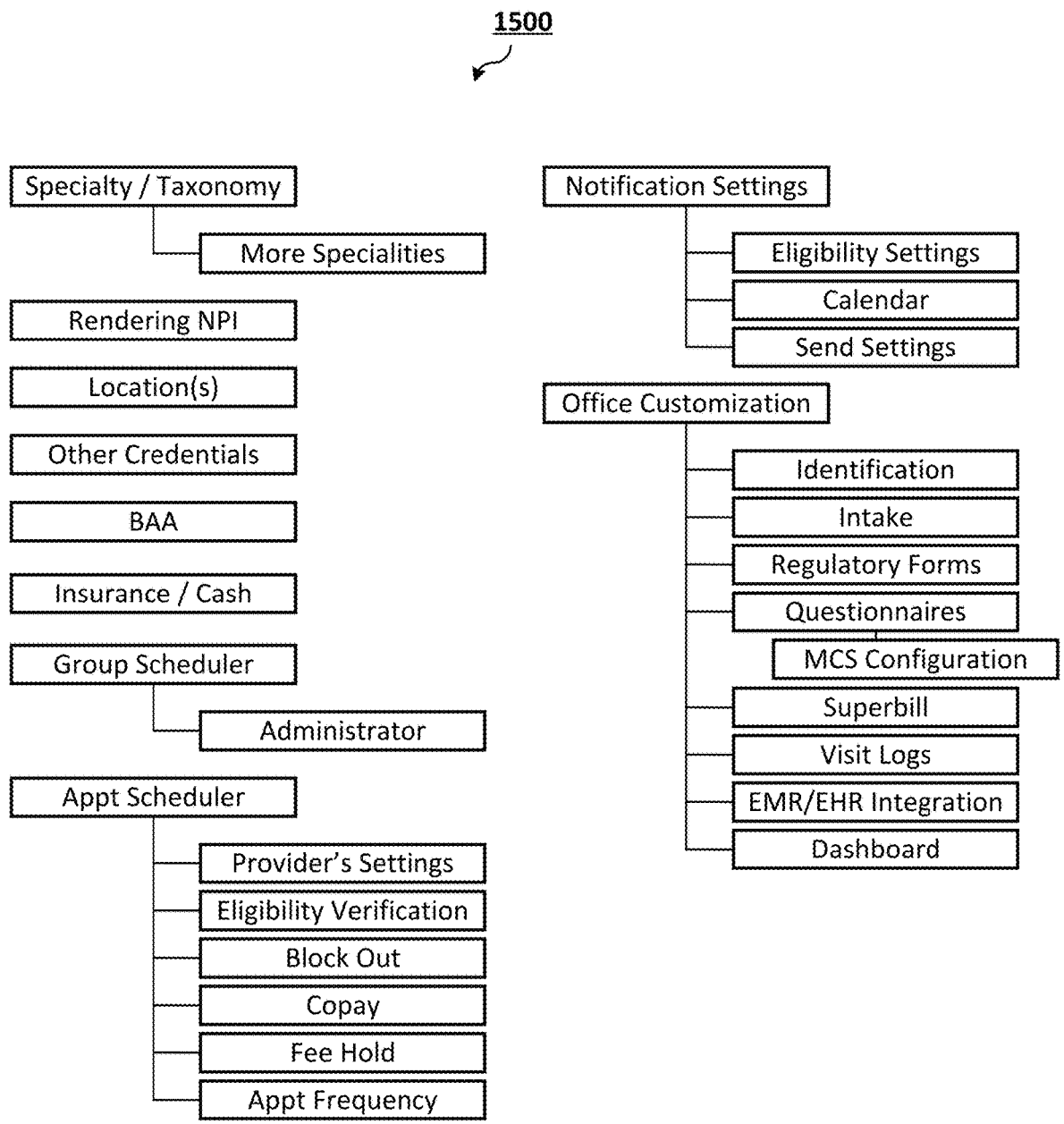
FIG. 15 is an exemplary configuration hierarchy for a health care group in association with the video conferencing system.

FIG. 15 is an exemplary configuration hierarchy for a health care group in association with the video conferencing system. As illustrated in FIG. 15, a health care group may have access to configuration settings of the video conference application. These configuration settings may include various settings related to appointment scheduling, office customization, notification settings, etc. The settings may be provided on an interface (e.g., a GUI) for a user of the health care group to configure. One skilled in the art will recognize that these are merely illustrative examples and that other alternative settings may be available as necessary or suitable for the medical care group.

Figure 16:
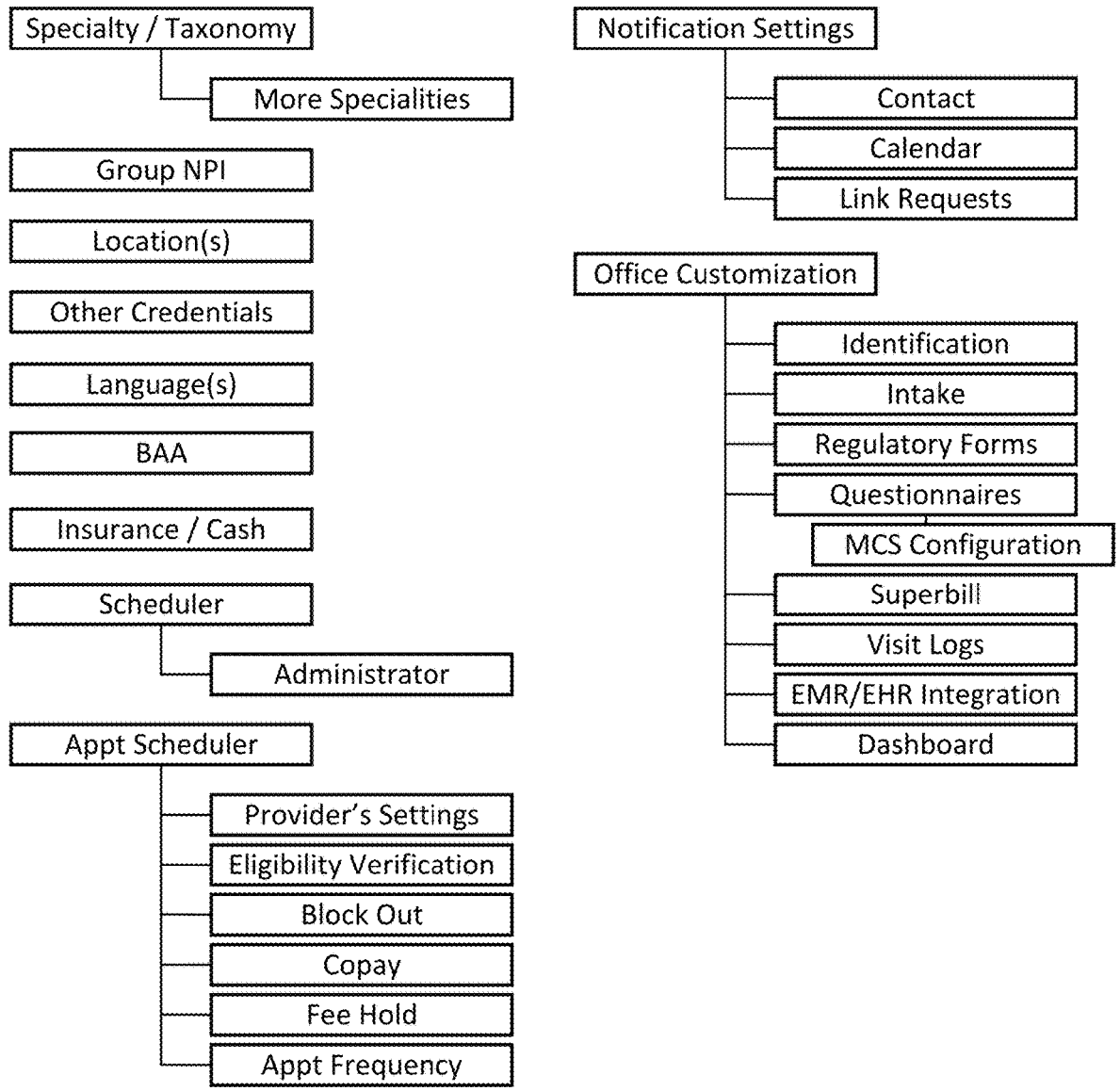
FIG. 16 is another exemplary configuration hierarchy for an individual health care provider in association with the video conferencing system.

FIG. 16 is another exemplary configuration hierarchy for an individual health care provider in association with the video conferencing system. As illustrated in FIG. 16, an individual care group may have access to configuration settings of the video conference application. These configuration settings may include various settings related to appointment scheduling, office customization, notification settings, etc. The settings may be provided on an interface (e.g., a GUI) for a user of the individual health care provider to configure. One skilled in the art will recognize that these are merely illustrative examples and that other alternative settings may be available as necessary or suitable for the medical care group.

Figure 17:
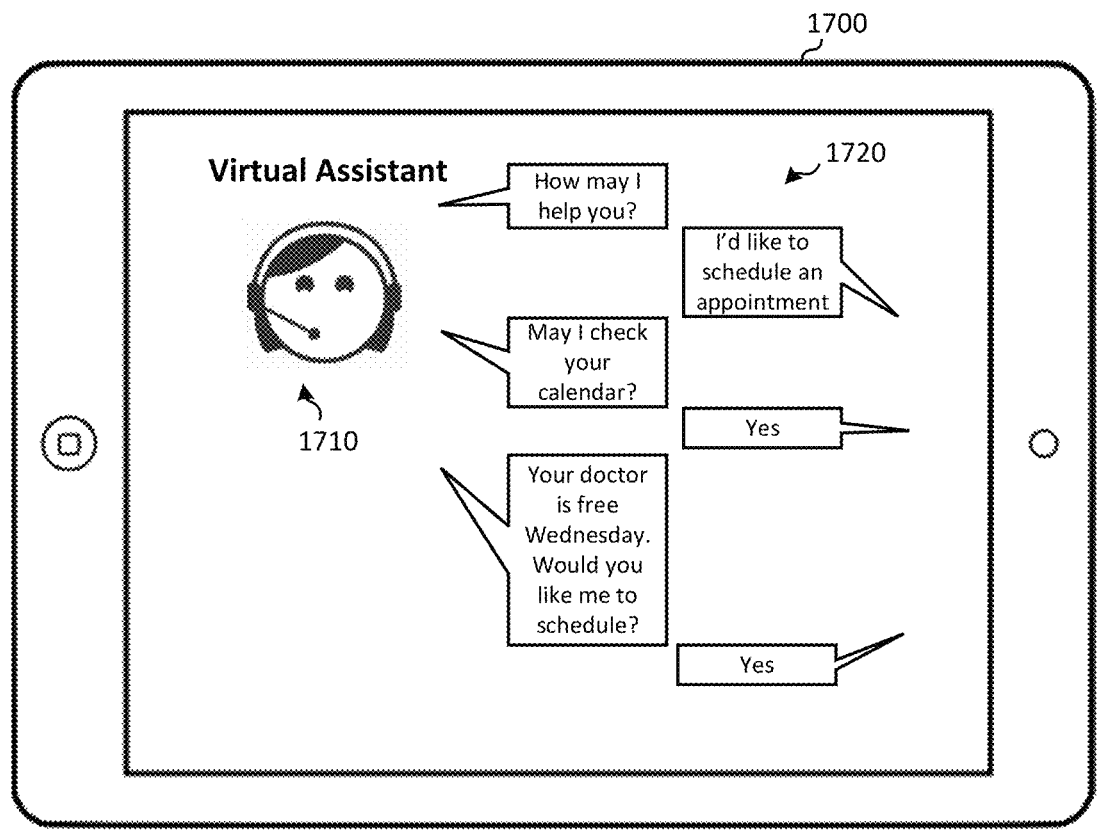
FIG. 17 is an exemplary diagram illustrating a display screen including a virtual assistant of the video conference participant device as viewed from a patient user of the system.

FIG. 17 is an exemplary diagram illustrating a display screen including a virtual assistant of the video conference participant device as viewed from a patient user of the system. In some embodiments, the video conference application may include virtual assistant features. For example, a virtual assistant may provide help in answering questions or setting up an appointment for medical checkup. In this context, a virtual assistant may be software and/or hardware configured to execute the methods described in the disclosure. In some embodiments, the virtual assistant may be augmented by a live person.

In the example of FIG. 17, the virtual assistant 1710 may include an avatar to provide a visual cue that the user is engaged with the virtual assistant. The virtual assistant may prompt 1720 the user for questions, and the assistant may continue a dialog with the user.

Figure 18:
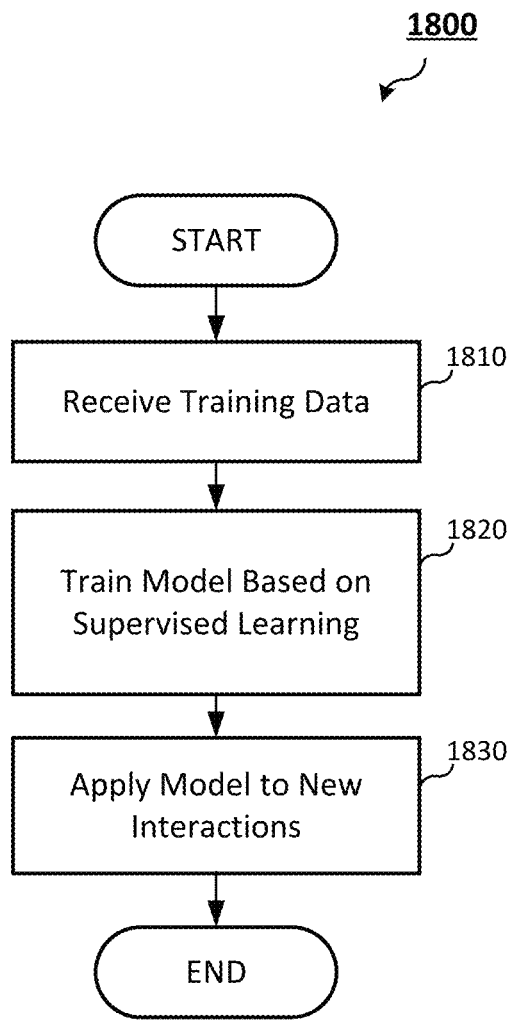
FIG. 18 is an exemplary flow diagram illustrating methods for training an artificial intelligence model for the virtual assistance of FIG. 17.

FIG. 18 is an exemplary flow diagram illustrating methods for training an artificial intelligence model for the virtual assistance of FIG. 17. The virtual assistant may be trained to interact with the user based on any one of a variety of artificial intelligence training methods. In the example of FIG. 18, the method may include, at step 1810, receiving training data (e.g., a large dataset with interactions between an assistant whether real or virtual and a typical user of the application). At step 1820, the method may include training a model based on any number of training methods such as a supervised learning process. At step 1830, the method may include applying the model to a virtual assistant of the video conferencing.

Figure 19:
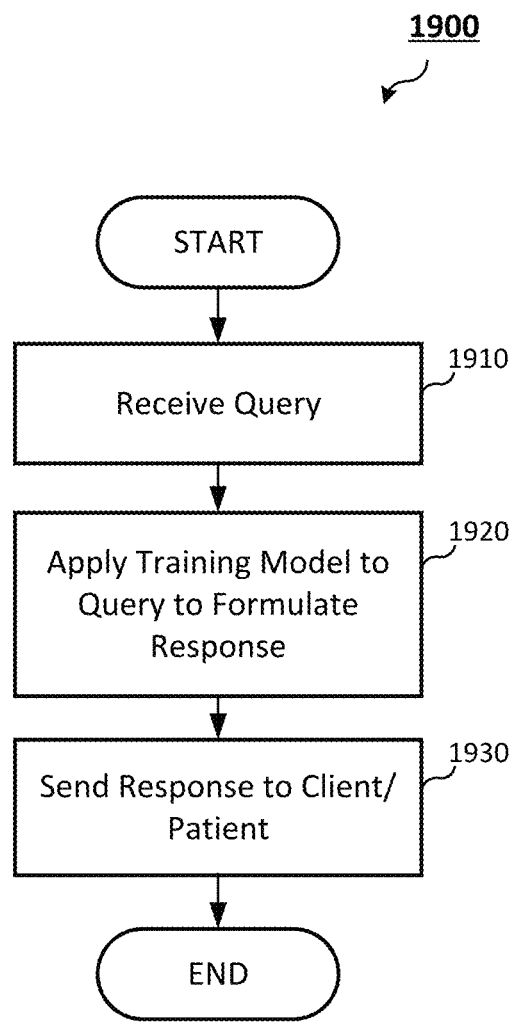
FIG. 19 is an exemplary flow diagram illustrating methods for applying the AI model created in FIG. 18 for the virtual assistance.

FIG. 19 is an exemplary flow diagram illustrating methods for applying the AI model created in FIG. 18 for the virtual assistance. The method may include, at step 1910, receiving a query, e.g., from a user of the application. For example, the user may have selected the virtual assistant feature. The virtual assistant feature may have appeared on-screen to prompt the user. The user may ask a question (e.g., a query) to the virtual assistant. At step 1920, the method may include applying the training model to the query to formulate a response. Based on the trained model, the virtual assistant may respond to the user. At step 1930, the method may include sending a response to the user or patient.

Some portions of the detailed descriptions above may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proved convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "receiving," "authenticating," "storing," "detecting," "retrieving," "granting," "performing," "locking," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the present invention also relate to an apparatus for performing the operations herein. This apparatus may be specifically constructed for the required purposes, or it may be general purpose computer system selectively programmed by a computer program stored in the computer system. Such a computer program may be stored in a computer readable storage medium, such as, but not limited to, any type of disk including optical disks, CD-ROMs, DVD-ROMs, Blu-ray disks, magnetic-optical disks, read-only memories (ROMs), random access memories (RAMs), EPROMs, EEPROMs, magnetic-optical disk storage media, optical storage media, flash memory devices, solid state devices, other type of machine-accessible storage media, or any type of media suitable for storing electronic instructions, each coupled to a computer system bus.

The algorithms and displays presented herein are not inherently related to any particular computer or other apparatus. In some embodiments various general-purpose systems may be used with programs in accordance with the teachings herein, or it may prove convenient to construct a more specialized apparatus to perform the required method steps. The required structure for a variety of these systems will appear as set forth in the description below. In addition, the present disclosure is not described with reference to any particular programming language. It will be appreciated that a variety of programming languages may be used to implement the teachings of the disclosure as described herein.

It is to be understood that the above description is intended to be illustrative, and not restrictive. Many other embodiments will be apparent to those of skill in the art upon reading and understanding the above description. Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

It is understood that the specific order or hierarchy of steps in the processes disclosed is an illustration of exemplary approaches. Based upon design preferences, it is understood that the specific order or hierarchy of steps in the processes may be rearranged. Further, some steps may be combined or omitted. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

What is claimed is:

1. A method implemented on a mobile video conference participant device, the method comprising:
   receiving a data packet via an encrypted electronic communication channel, the data packet comprising i) authorization from a server hosting privacy health care data and ii) scheduling information for a health care provider, wherein the scheduling information optionally includes mobile clinical staff (MCS) scheduler integration;
   creating a clickable link using the data packet, the clickable link configured for initiating a video conference session from a single user action on the clickable link;
   in response to the user pressing the clickable link:
      sending a second data packet to the health care provider for initiating the video conference session, and
      initiating the video conference session with the health care provider via a secure communication channel; and
   providing a game-like user interface during the video conference session with the health care provider for one of maintaining the user's attention or acquiring feedback regarding the user's state, wherein the game-like user interface comprises at least one user interface element including a flashing element.

2. The method of claim 1, further comprising receiving an acknowledgment of a log entry for the video conference session.

3. The method of claim 1, further comprising receiving an acknowledgment of a billing entry for the video conference session.

4. The method of claim 1, wherein the server hosting privacy health care data is an eligibility portal server comprising a database of patient eligibility records.

5. The method of claim 1, further comprising receiving a notification of an appointment prior to receiving the data packet.

6. The method of claim 5, further comprising:
   receiving user input indicating a scheduling conflict;
   receiving a preferred scheduling window for the appointment; and
   receiving a new appointment schedule from a remote server.

7. The method of claim 1, further comprising receiving at least one of a preference for a medical provider, a medical facility, a medical plan, a medical entitlement for services, or medical plan identification.

8. The method of claim 1, further comprising receiving user data comprising at least one of biographical information and medical information of the user.

9. The method of claim 1, further comprising transmitting the user data to a remote server, the user data being used by the remote server for the authorization of the health care services.

10. The method of claim 1, further comprising capturing interactive input from the user to maintain the attention of the user during the video conference session.

11. The method of claim 1, further comprising at least one biometric indicator of the user for transmission to a medical provider during the video conference session.

12. A method implemented on a server configured for scheduling video conference sessions, the method comprising:
   receiving data associated with a patient for medical services;
   receiving authorization from a server hosting a database comprising privacy health care data associated with the patient in response to a query for the customer's eligibility for medical services;
   determining scheduling information for the patient, wherein the scheduling information optionally includes mobile clinical staff (MCS) scheduler integration;
   creating a data packet for transmission over an encrypted electronic communication channel, the data packet comprising i) the authorization from the host server and ii) the scheduling information; and
   transmitting the data packet via the encrypted electronic communication channel for a remote video conference device to initiate a video conference session with a health care provider, wherein the video conference session provides a game-like user interface for one of maintaining a user's attention or acquiring feedback regarding the user's state, wherein the game-like user interface comprises at least one element including a flashing element.

13. The method of claim 12, further comprising receiving a request for the video conference session from a remote video conference device, the request comprising data associated with the data packet transmission.

14. The method of claim 12, further comprising initiating the video conference session with the remote video conference device via the secure communication channel.

15. The method of claim 12, wherein receiving authorization from the server is in response to querying an eligibility portal server comprising a database of patient eligibility records.

16. The method of claim 12, further comprising creating a log entry of the video conference session and a billing entry for the video conference session.

17. A method implemented on a mobile video conference participant device, the method comprising:
   receiving data associated with a patient for medical services;
   receiving appointment information for the patient for medical services, wherein the appointment information optionally includes mobile clinical staff (MCS) scheduler integration;
   receiving authorization, via an intermediate server, from an eligibility portal server hosting a database comprising privacy health care data associated with the patient in response to a query for the customer's eligibility for medical services;
   transmitting data to a remote mobile video conference participant device for configuring a video conference session associated with the appointment in response to receiving the authorization, wherein the video conference session provides a game-like user interface for one of maintaining a user's attention or acquiring feedback regarding the user's state, wherein the game-like user interface comprises at least one element including a flashing element.

18. The method of claim 17, further comprising initiating the video conference session in response to receiving a request from the remote video conference participant device.

19. The method of claim 18, further comprising receiving a selection of a split screen or single screen, the split screen including video of the patient and live biometric data of the patient captured on the patient's mobile video conference participant device.

20. The method of claim 17, further comprising creating a log entry for the video conference session and a billing entry for the video conference session.

* * * * *